United States Patent [19]

Meathrel et al.

[11] Patent Number: 5,665,477
[45] Date of Patent: Sep. 9, 1997

[54] HYDROGEL ADHESIVE FOR ATTACHING MEDICAL DEVICE TO PATIENT

[75] Inventors: William G. Meathrel, Buffalo, N.Y.; Mohammad Saleem, Gananoque; Shirley A. Binks, Ontario, both of Canada

[73] Assignee: Graphic Controls Corporation, Buffalo, N.Y.

[21] Appl. No.: 487,806

[22] Filed: Jun. 7, 1995

Related U.S. Application Data

[63] Continuation-in-part of Ser. No. 222,729, Apr. 4, 1994, Pat. No. 5,474,065.

[51] Int. Cl.$^6$ .............. B32B 27/30; A61L 25/00; B05D 5/10; C09J 4/02
[52] U.S. Cl. .............. 428/500; 128/640; 252/315.4; 252/518; 427/2.12; 427/207.1; 427/516; 428/461; 522/42; 523/177; 524/916; 526/317.1
[58] Field of Search .............. 128/640; 252/315.4, 252/518; 522/42; 523/177; 524/916; 526/317.1; 427/516, 207.1, 2.12; 428/500

[56] References Cited

U.S. PATENT DOCUMENTS

| | | |
|---|---|---|
| Re. 28,990 | 10/1976 | Hon et al. |
| 3,750,650 | 8/1973 | Ruttgers |
| 3,827,428 | 8/1974 | Hon et al. |
| 4,149,528 | 4/1979 | Murphy |
| 4,180,080 | 12/1979 | Murphy ................. 128/642 |
| 4,299,232 | 11/1981 | Zilanti ................. 128/642 |
| 4,301,806 | 11/1981 | Helfer ................. 128/642 |
| 4,308,873 | 1/1982 | Maynard ................. 128/642 X |
| 4,314,044 | 2/1982 | Hughes et al. ................. 524/808 |
| 4,320,764 | 3/1982 | Hon ................. 128/635 |
| 4,437,467 | 3/1984 | Helfer et al. ................. 128/642 |
| 4,458,696 | 7/1984 | Larimore ................. 607/152 |
| 4,515,162 | 5/1985 | Yamamoto ................. 128/640 |
| 4,577,635 | 3/1986 | Meredith ................. 128/642 |
| 4,602,640 | 7/1986 | Wada et al. ................. 128/639 |
| 4,658,825 | 4/1987 | Hochberg et al. ................. 128/634 |
| 4,706,680 | 11/1987 | Keusch et al. ................. 128/640 |
| 4,731,078 | 3/1988 | Stoy et al. ................. 623/6 |
| 4,825,879 | 5/1989 | Tan et al. ................. 128/633 |
| 4,921,904 | 5/1990 | Sparapany et al. ................. 525/329.9 |
| 4,934,371 | 6/1990 | Malis et al. ................. 128/642 |
| 4,938,218 | 7/1990 | Goodman et al. ................. 128/633 |
| 4,956,170 | 9/1990 | Lee ................. 514/772.1 |
| 4,989,607 | 2/1991 | Keusch et al. ................. 128/640 |
| 5,002,792 | 3/1991 | Vegoe ................. 128/639 X |
| 5,025,787 | 6/1991 | Sutherland et al. ................. 128/642 |
| 5,109,849 | 5/1992 | Goodman et al. ................. 128/633 |
| 5,124,076 | 6/1992 | Smuckler ................. 252/518 |
| 5,124,107 | 6/1992 | Schmid ................. 264/255 |
| 5,139,023 | 8/1992 | Stanley et al. ................. 128/637 |
| 5,143,071 | 9/1992 | Keusch et al. ................. 128/640 |
| 5,154,175 | 10/1992 | Gunther ................. 128/633 |
| 5,183,599 | 2/1993 | Smuckler ................. 264/22 |
| 5,183,841 | 2/1993 | Bernard ................. 524/272 |
| 5,184,619 | 2/1993 | Austin ................. 128/639 |
| 5,188,108 | 2/1993 | Secker ................. 128/633 |
| 5,217,013 | 6/1993 | Lewis et al. ................. 128/633 |
| 5,224,478 | 7/1993 | Sakai et al. ................. 128/633 |
| 5,254,338 | 10/1993 | Sakai et al. ................. 424/78.35 |
| 5,345,935 | 9/1994 | Hirsch et al. ................. 128/642 |
| 5,474,065 | 12/1995 | Meathrel et al. ................. 128/640 |

FOREIGN PATENT DOCUMENTS

| | | |
|---|---|---|
| 1103761 | 6/1981 | Canada . |
| 0099077 | 1/1984 | European Pat. Off. . |
| 0137500 | 4/1985 | European Pat. Off. . |
| 0248627 | 12/1987 | European Pat. Off. . |
| 0442011 | 8/1991 | European Pat. Off. . |
| 2569976 | 3/1986 | France ................. 128/612 |
| 2152808 | 4/1973 | Germany ................. 128/612 |
| 3816190 | 8/1989 | Germany ................. 128/612 |
| 9316259.6 | 3/1994 | Germany . |
| 4304693.2 | 8/1994 | Germany . |
| 91/07910 | 6/1991 | WIPO . |
| 91/15996 | 10/1991 | WIPO . |
| 92/04864 | 4/1992 | WIPO . |

OTHER PUBLICATIONS

N. J. Randall et al., Detection of the Fetal ECG During Labour by an Intrauterine Probe, 27th Annual Meeting of Biological Eng. Society, Oxford, UK, 2–4 Sep. 1987.

Okane et al., Non–invasive Continuous Fetal Transcutaneous $pO_2$ and $pCO_2$ Monitoring During Labor, J. Pernat. Med 17 (1989), pp. 399–410.

Schmidt, Glue Fixation of the $tcPco_2$ Electrode for Fetal Monitoring, J. Perinat. Med 15 (1987), pp. 377–382.

Hofmeyr et al., A Nonpenetrating Fetal Scalp Electrode, British Journal of Obstetrics and Gynaecology, vol. 100, pp. 649–652 (Jul. 1993).

*Primary Examiner*—Richard D. Lovering
*Attorney, Agent, or Firm*—Ratner & Prestia

[57] ABSTRACT

A biocompatible hydrogel adhesive which is prepared from a precursor containing acrylic acid and an alcoholamine and is adhesive under both wet and dry conditions. The use of diisopropanolamine provides these unexpected and unique wet tack properties and permits adhesion to wet tissue. Additionally, the use of a polyol which contains hydroxyl groups, such as glycerine, and a diamine, such as 2-methylpentamethylenediamine, is found to provide a hydrogel having wet adhesive properties and longer shelf life. The hydrogel adhesive can be used as an attachment means in conjunction with a biomedical detection or monitoring means. The adhesive may be used to attach a sensor on the skin of an intrautero fetus and to monitor the well being of the fetus during labor and delivery. The hydrogel having wet adhesive properties permits the attachment of a sensor or sensors onto wet tissue. The biocompatible adhesive is used to attach a fetal probe securely to a fetus. The adhesive can be used as an attachment means for a drug delivery or prosthetic device or as an attachment means for fixing a contraceptive device to the wall of the uterus. The attachment means could also be used in the oral cavity to fix a sensor or for oral therapies.

39 Claims, 8 Drawing Sheets

FIG. 12

HYDROGEL ADHESIVE FOR ATTACHING MEDICAL DEVICE TO PATIENT

This application is a continuation-in-part of application Ser. No. 08/222,729 filed Apr. 4, 1994, now U.S. Pat. No. 5,474,065.

FIELD OF THE INVENTION

The present invention relates to a biocompatible adhesive which adheres to wet skin. The adhesive may be used as an adhesive for wound care dressings, diaphoretic electrodes, vaginal drug therapies, and ostomy attachment appliances. More particularly, the invention relates to an electrically conductive biocompatible adhesive and biomedical sensing means, which utilize the adhesive, such as a fetal pulse oximeter and a non-invasive fetal probe which adhere to the skin of a fetus during labor and delivery.

BACKGROUND OF THE INVENTION

There is a need for a biocompatible adhesive which adheres to wet skin. Generally such an adhesive would be useful for use in attaching products which require or which would benefit from an adhesive with wet tack properties. Examples of such products are wound care dressings, diaphoretic electrodes, vaginal drug therapies, and ostomy attachment appliances.

Other applications requiring secure attachment means in a wet environment could also utilize such an adhesive. For example, such an adhesive would also be a useful alternative to securely attach equipment for biometric monitoring of fetal parameters (physical and chemical) intrautero during labor. During labor and delivery, the well-being of the fetus must be carefully monitored. The procedure of monitoring the fetus allows the clinician to assess the health of the fetus, detect fetal stress, and provide appropriate treatment. Many internal devices and methods are used to directly monitor and record such fetal parameters as heart rate, blood gas composition, and pH levels during labor and delivery. These direct monitoring procedures require a secure attachment of the sensor to the tissue of the fetus and commonly use sharpened wires in the form of spiral wires or hooks as the securing means. Examples of devices which evaluate the well being of the fetus by measuring fetal parameters are a fetal spiral electrode and a fetal pulse oximeter.

A fetal spiral electrode directly monitors fetal heart rate during labor using fetal scalp electrodes, such as those manufactured by Graphic Controls Corporation, having a sharpened helical wire for the secure attachment of the sensor. The wire penetrates the fetal tissue. Vacuum systems, inflatable balloons, and glue have been used to secure sensors to fetal skin. Active vacuum systems such as those described in U.S. Pat. No. 5,345,935 are bulky and are easily dislodged during labor. In addition, these systems restrict maternal mobility. Inflated balloons increase intrauterine pressure and the balloon may restrict fetal movement and maternal mobility. Prior art glues either do not adhere in a wet environment or, for adhesives such as the cyanoacrylates ("super glue"), aggressively bond the sensor to the skin so that removal requires cutting of the sensor from the tissue.

Fetal pulse oximetry is used to monitor the oxygen saturation in fetal tissue during labor and is described in German Patent Application Number P4304693.2 to Gerhard Rall and Reinhold Knitza. A fetal pulse oximeter is fixed to the fetal scalp by a sharpened helix wire similar to a fetal scalp electrode. This fetal pulse oximeter would be improved by the use of an attachment means which fixes the sensor to the fetal tissue without trauma. In addition, the wire attachment may affect the blood flow to the tissue at the site of attachment and therefore give an erroneous indication of fetal well being. A non-.invasive attachment means would be preferred.

Other diagnostic equipment, although not invasive, could also benefit from an adhesive having improved wet tack properties. For example, a transcutaneous fetal blood gas analysis for oxygen and carbon dioxide levels attaches sensors to a fetus by vacuum and "super glue" adhesives. Problems experienced with these sensors include bulky vacuum systems which cause the sensor to dislodge and also trauma to the skin by the cyanoacrylate adhesives. Other prior art pressure-sensitive adhesives, such as those used for self-adhesive bandages, cannot be readily utilized for such an application as they are hydrophobic and will not adhere to wet surfaces such as fetal skin.

Glue fixation of a transcutaneous $pCO_2$ electrode for fetal monitoring has been described by S. Schmidt, "Glue fixation of the $tcPco_2$ electrode for fetal monitoring," Journal Perinatal Medicine, 15(4), 377 (1987). Glue fixation to a fetus is difficult to achieve. It requires sufficient dilation and careful preparation of the attachment site. The electrode often becomes detached during use and may need to be reapplied. In addition, trauma to the skin during removal of a sensor attached by glue is possible. If the sensor is not completely sealed to the tissue, air leakage under the seal will cause an erroneous indication of oxygen and carbon dioxide levels. A biocompatible adhesive hydrogel with wet adhesive properties would be preferred as the attachment means.

An adhesive with wet tack properties could also be used for the attachment of sensors in the oral cavity. U.S. Pat. No. 5,139,023 discloses a non-invasive blood glucose sensor which attaches to the epithelial membrane. Bioadhesive hydrogels such as cellulose and cellulose derivatives, CARBOPOL polymer and gelatin are utilized as the attachment means. These materials are not sufficiently adhesive or stable, however, to allow a durable attachment. In addition, bioadhesives such as the polycarbophil resins available from B. F. Goodrich under the trademark NOVEON have been used for vaginal drug therapies. These materials may not have the adhesive properties or durability required for long term application.

To overcome the shortcomings of prior art attachment means, a new hydrogel with wet adhesive properties is provided.

SUMMARY OF THE INVENTION

The present invention provides a biocompatible hydrogel adhesive which adheres to wet tissue. The use of an alcoholamine such as diisopropanolamine provides these unexpected and unique wet tack properties. Additionally, the use of a polyol which contains hydroxyl groups, such as glycerine, and a diamine is found to provide a hydrogel having wet adhesive properties and longer shelf life. Preferably, the hydrogel adhesive can be used as an attachment means in conjunction with a biomedical detection or monitoring means. The adhesive may be used to attach a sensor on the skin of an intrautero fetus and to monitor the well being of the fetus during labor and delivery. The hydrogel having wet adhesive properties permits the attachment of a sensor or sensors onto wet tissue. Preferably, the biocompatible adhesive of the present invention is used to attach a fetal probe securely to a fetus in a non-invasive manner.

In addition, the adhesive can be used as an attachment means for a drug delivery therapy or prosthetic device. The adhesive may also be used as the attachment means for fixing a contraceptive device to the wall of the uterus. The attachment means could be used for vaginal therapies such as drug delivery and for the attachment of vaginal or transvaginal sensors. The attachment means could also be used in the oral cavity to fix a sensor or for oral therapies.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing, in which.

DETAILED DESCRIPTION OF THE INVENTION

I. Wet Adhesive Hydrogel Formulations and General Uses

Polymeric hydrogels can be soft and flexible materials. Hydrogels exhibit shape memory and will return to their original shape even after deformation. Hydrogels also have the important characteristics of biocompatibility, hydrophilicity (the ability to absorb water), and may have adhesive properties, and electrical conductivity - - - they mimic characteristics of living tissue.

Hydrogels can be polymerized into many desirable shapes. One characteristic of hydrogels is their shape retention property. Suction cups with wet adhesive properties have been formed by the polymerization of hydrogel formulations containing acrylic acid and solutions of acrylic acid or an acrylic acid salt and a second monomer. In addition to an acrylic acid component, the formulation also contains an alcoholamine or a diamine which is able to react with the acrylic acid component to form a monomer with a pendant side chain containing a nitrogen atom. A general formulation for these compounds is shown below:

where:

$R^I$, $R^{IV}$, $R^C$=H or alky $R^{II}$, $R^{III}$=H or C x=

OH, or halogen y=1 to 6

It is found that the use of diisopropanolamine provides these unexpected and unique wet adhesive properties. It is theorized, although not intending to be limited by such theory, that the good wet adhesive properties result from a nitrogen atom in the polymer chain pendant group which helps to provide the required surface energy to interact with the wet surface such as fetal tissue wetted with amniotic fluid.

Additionally, the use of a polyol, such as glycerine, and a diamine which contains hydroxyl groups, such as 2-methylpentamethylenediamine, is found to provide a hydrogel having wet adhesive properties and longer shelf life.

Suitable hydrogel formulations which can be polymerized to form hydrogels according to the present invention with good wet adhesive properties are given in the following table.

TABLE 1

|  | Example 1 | Example 2 | Example 3 | Example 4 | Example 5 |
| --- | --- | --- | --- | --- | --- |
| potassium chloride | 3.0 | 3.50 | 3.50 | 3.50 | 3.50 |
| water | 29.2 | 38.96 | 35.05 | 38.91 | 27.50 |
| glycerine | 14.24 | — | — | — | 26.38 |
| potassium polyacrylate | 4.2 | — | — | — | — |
| diisopropanolamine | 24.15 | 28.12 | 30.00 | 28.12 | — |
| acrylic acid | 24.9 | 28.97 | 17.81 | 15.97 | 25.00 |
| initiator (Darocur 1173) | 0.35 | 0.35 | 0.35 | 0.35 | 0.35 |
| PEGDA | 0.10 | 0.10 | 0.10 | 0.15 | 0.125 |
| hydroxyethylmethacrylate | — | — | 13.19 | — | — |
| vinyl pyrrolidone | — | — | — | 13.00 | — |
| 2-methylpentamethylenediamine | — | — | — | — | 17.14 |

Each of the polymers formed in the hydrogel compositions in Table 1 can be a homopolymer of acrylic acid, copolymer of acrylic acid and acrylic acid salts, copolymers of acrylic acid and esters derived from alcoholamines, copolymers of acrylic acid and vinyl pyrrolidone, copolymers of acrylic acid and acrylates, and terpolymers of acrylic acid, acrylic acid salt, and an ester derived from the reaction of acrylic acid with the alcoholamine, and polymers obtained from any of the above monomer combinations. Darocur 1173 (2-hydroxy-2-methyl-1-phenyl-propane-1-one) is a photoinitiator available from Ciba Geigy. Polyethylene glycol (400) diacrylate (PEGDA) is a crosslinking agent available under the trademark Sartomer® 344, available from the Sartomer Company of West Chester, Pa. Glycerine is a humectant and plasticizer which provides flexibility and dry tack properties. Diisopropanolamine, a humectant and plasticizer, helps to neutralize the acid and gives the hydrogel good wet adhesive properties. Sodium hydroxide is added to control pH. Potassium chloride is an electrolyte which increases conductivity.

The preferred hydrogel compositions contain an alcoholamine such as diisopropanolamine. Hydrogel compositions have been prepared which include other secondary and tertiary alcoholamines such as triethanolamine and diethanolamine. These compositions also have good wet adhesive properties. Additionally, the use of a polyol which contains hydroxyl groups, such as glycerine, and a diamine, such as 2-methylpentamethylenediamine, and is found to provide a hydrogel having wet adhesive properties.

Thus, two important aspects of the present invention are 1) the chemical formulation of the hydrogel material used which imparts wet adhesive properties and 2) the various configurations which can be made from the hydrogel material itself to be used as an attachment means. An additional aspect is the use of a body made of the hydrogel material in combination with a fetal probe delivery system having a small diameter delivery tube. This delivery system allows for earlier application of the probe during labor due to the memory retentive properties of the body which allow it to be used with the smaller diameter delivery tube. A further aspect is the use of a body made of the hydrogel material in a non-invasive fetal pulse oximeter which does not cause trauma to the fetal skin.

The hydrogel compositions of the present invention may be made conductive or non-conductive as required by the application. The examples shown include an ionizable salt (i.e., potassium chloride) which enhances the ionic conductivity of the hydrogel. In many applications ionic conductivity would not be required and could be eliminated. Applications such as vaginal drug delivery and intrauterine therapies would not require a conductive hydrogel. The wet adhesive force of the hydrogel must be sufficient to hold a sensor or therapeutic device in place while allowing easy removal by the patient or clinician.

II) Non-Invasive Fetal Probe Using the Wet-Adhesive Hydrogel

One embodiment which incorporates the hydrogel compositions of the present invention is a non-invasive fetal probe which adheres biomedical sensors to the skin of a fetus during labor. The probe includes a conductive assembly, made from a hydrogel composition, which is formed into a body and then polymerized.

The use of the hydrogel material of the present invention provides several advantages over the prior art. First, because hydrogels have memory retention properties, the probe can be used with a smaller diameter guide tube (the body can be deformed before insertion). As a result, the fetal probe can be attached to the presenting part of the fetus earlier in labor; insertion of the smaller diameter delivery tube facilitates insertion of the probe.

Another advantage of the use of a hydrogel body to adhere the fetal probe is that, in addition to having good dry adhesive properties, certain hydrogel formulations impart enhanced wet adhesive properties to the fetal probe. The use of diisopropanolamine provides these unexpected and unique wet tack properties.

The adhesive properties achieved by the probe of the present invention avoid the attachment problems of the prior art. For example, the invasive technique of attaching an electrode having a sharp hook or wire directly to the fetal epidermis, with its concomitant risks of injuring the fetus and spreading diseases and viruses, is avoided. The accurate readings afforded by the present invention also improve the quality of the results obtained relative to such prior art external monitoring techniques and other techniques which, although non-invasive, do not securely and releasably attach a probe to the fetus.

A non-invasive fetal heart rate sensor is described in U.S. patent application Ser. No. 08/222,729, (now U.S. Pat. No. 5,474,065), the specification of which is incorporated by reference. In that application the hydrogel having wet adhesive properties of the present invention was incorporated into a sensor in the shape of a suction cup which attaches to a fetus intrautero to monitor the fetal heart rate during labor. The salient features of such a probe are described below.

Figure 1:
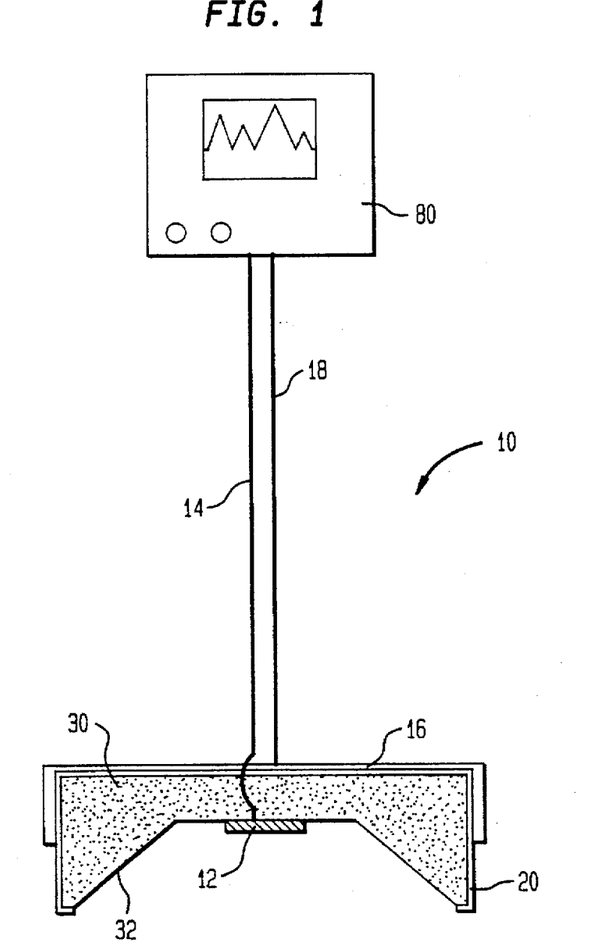
FIG. 1 is a cross section of a non-invasive fetal probe constructed in accordance with the present invention.
Figure 2:
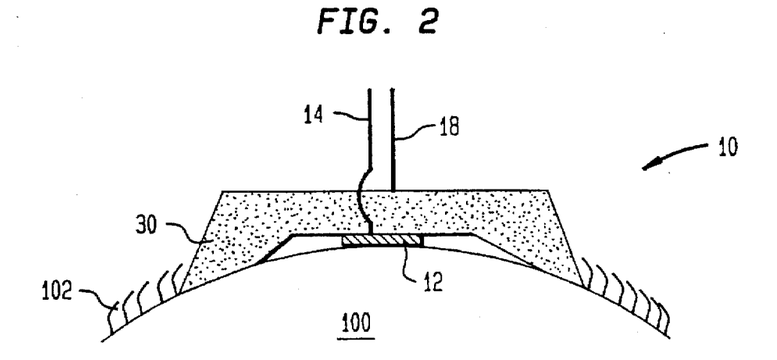
FIG. 2 is a cross section of the fetal probe shown in FIG. 1 attached to a fetus.
Figure 3:
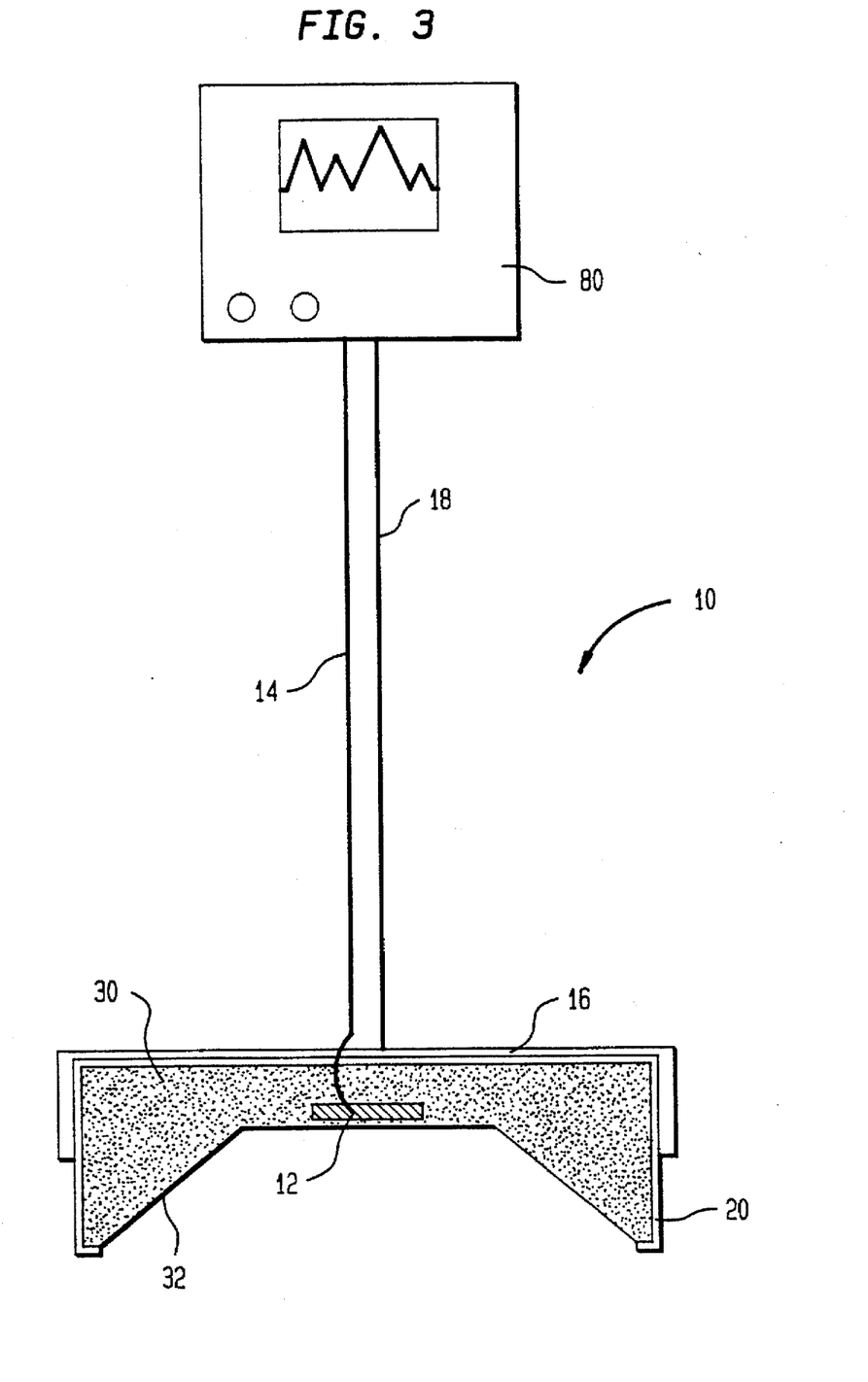
FIG. 3 is a cross section of the fetal probe of the present invention having a fetal sensor embedded in the hydrogel of the body of the fetal probe.

Referring now to FIGS. 1 to 9, wherein like reference numerals refer to like elements, FIGS. 1, 2, and 3 illustrate a non-invasive fetal probe 10 constructed in accordance with the present invention. It is emphasized that, according to common practice, the various elements of the drawing are not to scale. On the contrary, the width, length, and thickness of the various elements are arbitrarily expanded or reduced for clarity.

Fetal probe 10 is inserted through the birth canal and is attached to the presenting part (typically the head) of the fetus 100. Because it is "non-invasive," fetal probe 10 does not penetrate the fetal skin. Once attached, fetal probe 10 can continuously sense, depending upon the sensors incorporated in fetal probe 10, such fetal parameters as heart rate, blood gas composition, temperature, and pH levels during labor and delivery. Other types of sensors and test equipment or combinations of sensors and test equipment could be incorporated into fetal probe 10.

Fetal probe 10 has a fetal sensor 12 with an attached fetal sensor connector 14. A maternal sensor 16 and attached maternal sensor connector 18 may also be provided. Fetal sensor 12 and maternal sensor 16 are electrodes, and fetal connector 14 and maternal connector 18 are electric leads, when fetal probe 10 is a fetal heart rate probe. In that case, an insulating barrier 20 maintains electrical separation between fetal sensor 12 and maternal sensor 16. Maternal sensor 16 can be positioned on the top surface of probe 10 or may extend down the sides of probe 10. A body 30 provides the base to which fetal sensor 12 and maternal sensor 16 are attached and secures fetal probe 10 to fetus 100.

As shown in FIG. 1, fetal sensor 12 may be positioned on the surface of body 30. Alternatively, as shown in FIG. 3, fetal sensor 12 may be embedded in body 30. In either case, fetal sensor connector 14 and maternal sensor connector 18 connect fetal sensor 12 and maternal sensor 16, respectively, to an external monitor 80.

A. Composition of Fetal Probe Body

Various compositions can be used to make a hydrogel suitable for body 30. Example compositions (by percentage) are listed in Table 2. Example 2 corresponds to example 2 in Table 1 and shows a preferred embodiment for substantially hairless fetal skin. Examples 1, 3, and 4 show additional compositions utilizing diisopropanolamine for wet tack properties. Example 4 is a preferred embodiment for fetal skin with a significant amount of hair.

TABLE 2

| Component | Ex. 1 | Ex. 2 | Ex. 3 | Ex. 4 |
| --- | --- | --- | --- | --- |
| Water | 24.82 | 38.96 | 10.7 | 37.56 |
| Acrylic Acid | 19.13 | 28.97 | 21.7 | 15.97 |
| Darocur 1173 | 0.35 | 0.35 | 0.33 | 0.35 |
| Polyethylene Glycol (400) Diacrylate | 0.10 | 0.10 | 0.17 | 0.15 |
| Glycerine | 46.80 | — | 27.8 | — |
| Colloid 121 | — | — | 14.9 | — |
| Diisopropanolamine | 7.80 | 28.12 | 13.8 | 28.12 |
| Sodium Chloride | 1.00 | — | — | — |
| Potassium Chloride | — | 3.50 | 1.0 | 3.50 |
| 27% Aqueous Sodium Hydroxide | — | — | 9.6 | — |
| Vinyl Pyrrolidone | — | — | — | 13.00 |

Each of the polymers formed in the hydrogel compositions in Table 2 can be a homopolymer of acrylic acid, copolymer of acrylic acid and acrylic acid salts, copolymers of acrylic acid and esters derived from alcoholamines, copolymers of acrylic acid and vinyl pyrrolidone, copolymers of acrylic acid and acrylates, and polymers obtained from any of the above monomer combinations. In the case of a fetus with significant amounts of hair, a formulation made with 13 percent of vinyl pyrrolidone is the preferred embodiment (Example 4). Darocur 1173 (2-hydroxy-2-methyl-1-phenyl-propane-1-one) is a photoinitiator available from Ciba Geigy. Polyethylene glycol (400) diacrylate is a crosslinking agent available under the trade name Sartomer® 344, available from the Sartomer Company of West Chester, Pa. Glycerine is a humectant and plasticizer which provides flexibility and dry tack properties. Colloid 121, a polyacrylic acid solution available from Rhone-Poulenc in Marietta, Ga., enhances wet tack, viscosity, and formability properties. Diisopropanolamine, a humectant and plasticizer, helps to neutralize the acid and gives the hydrogel good wet adhesive properties. Sodium hydroxide is added to control pH. Sodium chloride and potassium chloride are electrolytes which increase conductivity.

The preferred hydrogel composition contains an alcoholamine such as diisopropanolamine. Hydrogel compositions have been prepared, however, including other secondary and tertiary alcoholamines such as triethanolamine and diethanolamine. These compositions also have good wet adhesive properties.

U.S. Pat. No. 4,921,904 (Sparapany et al.) describes super-absorbant hydrogels which include a polyamine. Diisopropylamine is mentioned. Diisopropylamine is not the same chemical, however, as diisopropanolamine. Polyamines have a single functional atom, the nitrogen atom, whereas alcoholamines have at least two functional sites - - - a nitrogen atom and a hydroxyl group.

U.S. Pat. No. 5,124,076 and U.S. Pat. No. 5,183,599 issued to Smuckler teach a hydrogel adhesive composition for medical electrodes which polymerizes rapidly, preferably in less than ten seconds. Specifically, the hydrogel composition contains-a mixture of an N-vinyl lactam and an acrylate monomer. The hydrogel compositions of the present invention use a single monomer, acrylic acid, or a copolymer of acrylic acid and vinyl pyrrolidone, and the polymerization time (although rapid) is of little importance.

During labor, the intrapartum fetus is exposed to amniotic fluid, vaginal fluids, and, in some cases, fetal excretions. In this wet environment, an adhesive with good wet tack properties is required. (The tack is the characteristic of the adhesive to stick to a surface.) The hydrogels produced by curing the compositions listed as Examples 1–4 in Table 2 exhibit the unique property of having both a dry and a wet tack. The alcoholamine (and, specifically, diisopropanolamine) used in the compositions provides this property.

Many adhesives, for example pressure sensitive adhesives which are used with adhesive tapes, exhibit good adhesive properties to dry surfaces. These adhesive tapes, however, typically do not adhere well to wet surfaces. U.S. Pat. No. 5,139,023 issued to Stanley et al. describes a blood glucose sensor which uses a hydrogel (hydroxypropyl cellulose, gelatin, and CARBOPOL polymer) to adhere the device to mucosal membranes. Such materials are unlikely to have sufficient adhesive properties to hold a device such as fetal probe 10 to a wet surface such as fetus 100.

The hydrogel compositions of the present invention also have shape memory. The shape memory characteristic enables body 30 to return to the desired concave suction-cup shape after deformation. The great flexibility of the hydrogel also allows body 30 to form a strong suction when pressed against the epidermis of fetus 100.

The attachment force which holds fetal probe 10 in place on fetus 100 must be sufficient to hold fetal probe 10 in place during labor. An attachment time of ten hours or more may be required. Further, fetal probe 10 must adhere even if fetus 100 has hair 102.

Figure 4:
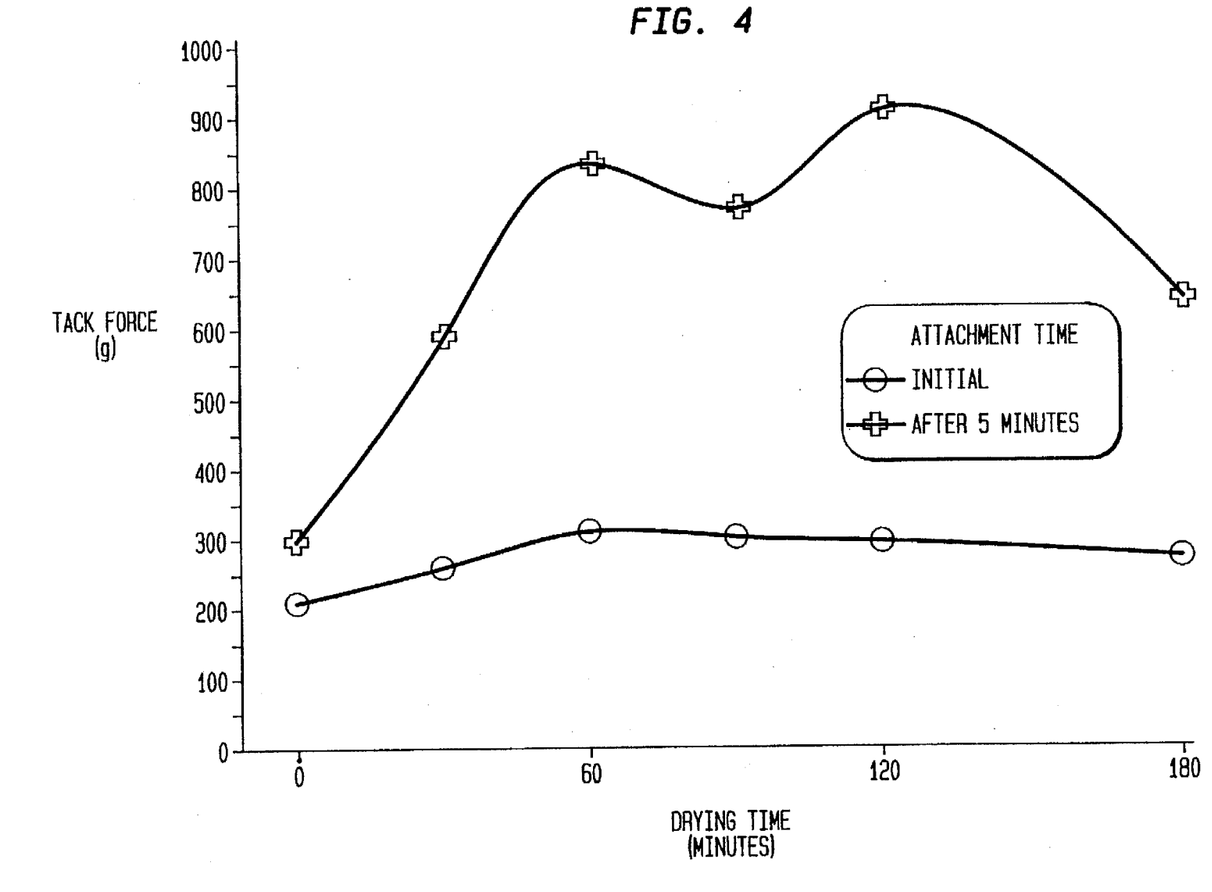
FIG. 4 is a graph of tack force (g) versus drying time (minutes) illustrating the effect of drying the hydrogel composition of Example 3, Table 1, on adhesion.

It has been found that drying the hydrogel, Example 2, Tables 1 and 2 to remove some of the water from the polymer matrix can increase the tack of the hydrogel on hairy skin. FIG. 4 shows the effect of drying time on adhesion. Moreover, hydrogels prepared using vinyl pyrrolidone provide added adhesion to hairy tissue. Increased adhesion to hairy tissue has been found by replacing approximately half of the acrylic acid monomer with vinyl pyrrolidone (see Example 4 of Table 2).

Because body 30 may be used as a conductive pathway of electrical signals between fetus 100 and fetal sensor 12, body 30 must be electrically conductive as well as adhesive. The hydrogel compositions used to form body 30 meet that requirement. The hydrogel compositions of Table 2 have a 10 Hz impedence less than or equal to 2000 ohms to an impressed current of 100 microamperes. Thus, the physical and electrical properties of the hydrogel compositions can be controlled to provide a flexible, conductive, adhesive interface between fetus 100 and fetal sensor 12.

Each of the compositions listed in Table 2 may be polymerized by various means, such as ultraviolet light, heat, electron beam, redox reagents, and the like. Exposure to ultraviolet radiation is the preferred way to initiate polymerization. The hydrogel composition may be used "as is," in its form following polymerization, or the composition may be cast as a coating and then dried to provide a flexible, non-tacky, thermoplastic film.

Alternatively, the composition may be polymerized directly into a non-tacky, flexible sheet. This dry coating, flexible sheet can then be formed into the desired shape (such as a suction cup). The dry coating can be "wetted" to regain its dry and wet adhesive properties. Using the polymer as a non-tacky, dry coating on fetal probe 10 can allow for easy insertion of fetal probe 10 through the birth canal. Once in place, fluids around the fetus will reactivate the adhesive properties of the hydrogel and hold fetal probe 10 in place.

The applications for a hydrogel having good wet and dry adhesive properties are broader than a non-invasive fetal probe 10. Applications such as wound dressings and closures, transdermal drug delivery systems, ostomy adhesive's, medical tapes, various medical electrodes, and the like could benefit from a hydrogel adhesive with wet and dry adhesive properties.

B. Configuration of Fetal Probe Body

The hydrogel compositions of the present invention can be molded or formed to provide almost any desired size and shape. Body 30 can be formed by dispensing the hydrogel composition into a mold of the desired shape then polymerizing the monomers in the mold. Alternatively, suction cup-shaped probes can be prepared by spin casting, similar to the procedure used to prepare soft contact lenses.

Although the present invention contemplates the use of a hydrogel body having a flat adhering surface, a suction cup body can be utilized as described in U.S. patent application Ser. No. 08/222,729 (now U.S. Pat. No. 5,474,065). Suction cups are commonly used to attach items to flat surfaces. The attachment is achieved by creating a negative pressure between the flat surface and the inner, concave surface of the suction cup. The bond between the flat surface and the concave surface of the suction cup depends both upon the composition, shape, and area of the suction cup and upon the characteristics of the flat surface such as smoothness and porosity. The bond fails when the negative pressure between the two surfaces is increased to atmospheric pressure. That occurs when air leaks under the edges of the suction cup or diffuses through the suction cup into the small gap formed between the flat surface and the concave surface of the suction cup.

Strong, durable bonds between suction cups and smooth, rigid, flat surfaces such as glass can be formed by the creation of strong Van der Waals' forces due to the close proximity of the two surfaces. Moreover, suction cups adhere better to wet surfaces because the water reduces surface texture and, therefore, increases Van der Waals' interactions. On fetal skin, however, which is pliable, textured, and curved, conventional suction cups will not adhere for sufficient time to be useful for fetal monitoring applications. They fall off almost immediately when applied to fetal skin.

Fetal probe 10 of the present invention solves that problem in two ways. First, the material or composition of body 30 of fetal probe 10 is designed to provide adhesion between body 30 and fetus 100. Second, the configuration of body 30 is a suction cup designed to facilitate adhesion between suction cup 30 and fetus 100. The initial attachment of fetal probe 10 to the wet surface of fetus 100 uses the vacuum created by the suction cup configuration of body 30. Thereafter, the material used to form body 30 absorbs the moisture of the wet environment, creating strong surface adhesive properties between body 30 and the skin of fetus 100.

The size and shape of body 30 formed by the hydrogel composition of the present invention affects the adhesion between body 30 and fetus 100. A suction cup shape for body 30 having a concave surface 32 contacting fetus 100 is preferred to enhance adhesion. Table 3 compares various shapes and diameters possible for body 30 and provides the 90-degree peel (the force required to peel body 30 from a flat, stainless steel plate) for each particular shape and diameter. A Shimpo Digital Force Gauge Model DF-5.OR (supplied by Shimpo America corporation of Lincolnwood, Ill. 60659) was used to make the measurements contained in Table 3.

TABLE 3

| Shave | Diameter (mm) | 90° Peel Force (g) |
|---|---|---|
| Concave U | 15 | 400 |
| Concave V | 15 | 450 |
| Concave V | 20 | 710 |
| Concave V | 50 | >1075 |
| Flat | 20 | 360 |
| Convex | 30 | 720 |

Table 3 indicates that a shallow, V-shaped cup is more difficult to remove than a deeper, U-shaped cup. This additional adhesive power is beneficial toward maintaining contact during labor. Larger surfaces also have higher 90-degree peel strengths. Finally, cups with a concave shape require more force to remove them than flat and convex-shaped cups of similar size.

It is desirable for a fetal probe 10 to have a small enough diameter for ease of application early in labor. For example, a V-shaped, concave cup with a diameter of 15 to 20 mm, or which can be collapsed into a dispenser or guide tube of this diameter or less, is preferred. Such a size permits application of fetal probe 10 when cervical dilation is 1 cm or less. Fetal probe 10 need not be collapsed for insertion, as it can be placed inside a delivery tube or applied with other delivery means in an uncollapsed state.

Figure 5:
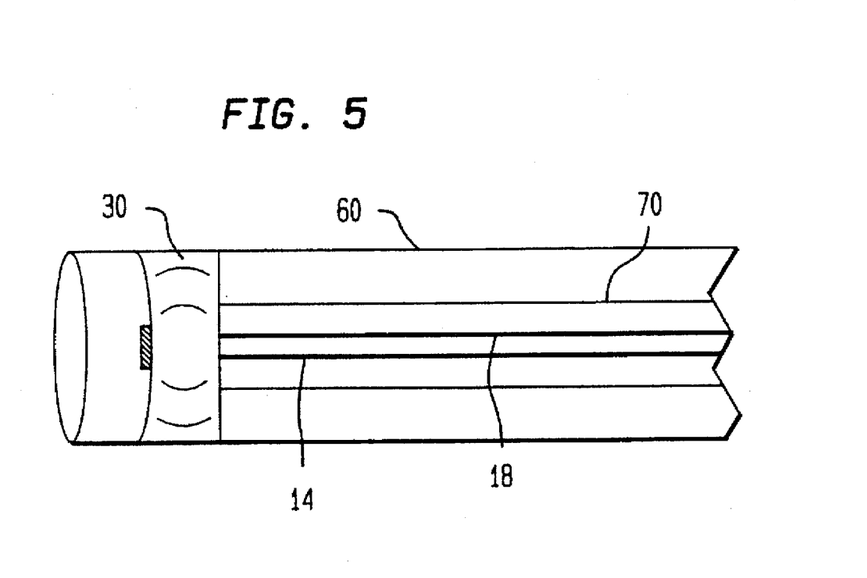
FIG. 5 is a cross section of the non-invasive fetal probe of FIGS. 1 or 3 disposed inside a guide tube in a collapsed state.

To assure both applicability of fetal probe 10 early in labor and maximum adhesive strength (larger surfaces provide more strength), the shape-retention property of hydrogel proves useful. FIG. 5 shows an exemplary embodiment of fetal probe 10 disposed inside a guide tube 60. Guide tube 60 may have a diameter of 20 mm while body 30 of fetal probe 10 has a diameter of 40 mm. Accordingly, fetal probe 10 is collapsed within guide tube 60. It will be understood that the sizes for both fetal probe 10 and guide tube 60 (or other delivery means) can be made smaller or larger, depending upon the application as will be understood by those skilled in the art.

Figure 6:
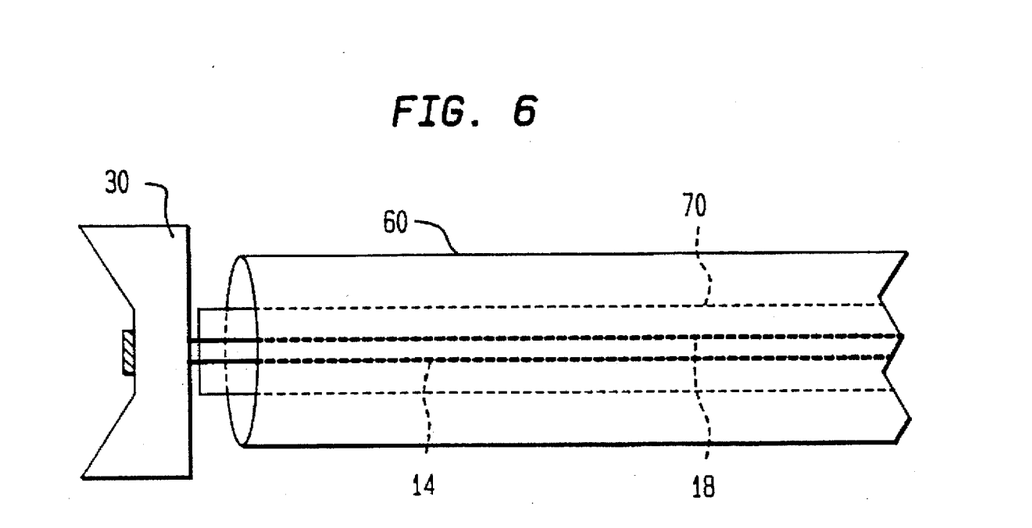
FIG. 6 is a cross section of the non-invasive fetal probe of FIGS. 1 or 3 in its normal expanded state outside of the guide tube and following expulsion from the guide tube.

Drive tube 70, which has a smaller diameter than guide tube 60, may be used to push fetal probe 10 out of guide tube 60. Once removed from guide tube 60, body 30 of fetal probe 10 regains-through the shape retention properties of the hydrogel used to form body 30 - - - its initial, uncollapsed shape. FIG. 6 shows fetal probe 10 following ejection from guide tube 60.

In FIG. 6, it can be seen that fetal probe 10 has regained its desired, initial shape and is ready for attachment to the fetal skin. Thus, the deformation of fetal probe 10 while disposed inside guide tube 60 does not affect the shape at the time of attachment to fetus 100. Other methods of placing fetal probe 10 into contact with fetus 100 will be understood by those skilled in the art.

Body 30 may be formed entirely of hydrogel. Alternatively, body 30 may be formed of another material and only concave surface 32 of body 30 coated with a hydrogel composition of the present invention. Fetal probe 10 having body 30 so constructed shows satisfactory adhesive properties to fetus 100.

Figure 7:
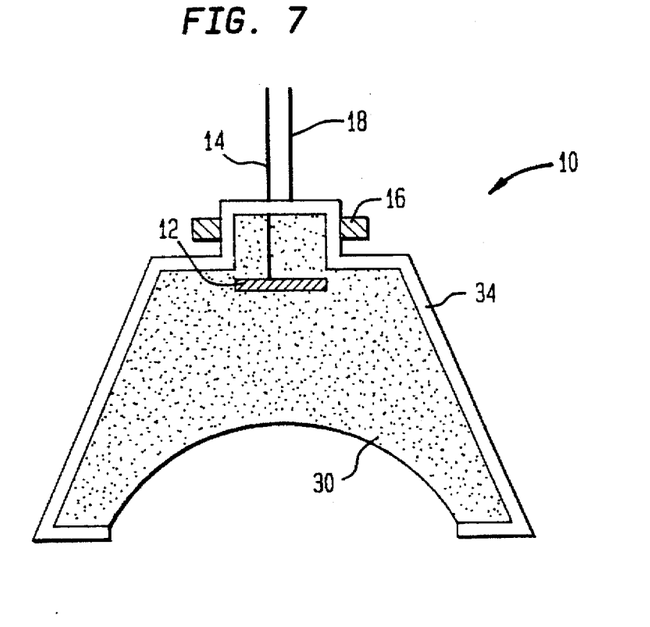
FIG. 7 is a cross section of an additional embodiment of a non-invasive fetal probe having a shell coated with hydrogel.

FIG. 7 depicts a thermoplastic shell 34 coated with hydrogel to form body 30. Shell 34 can be formed by a number of processes understood by those skilled in the art, including molding. Suitable dimensions for shell 34 are a total height of about 6.2 mm and a diameter of about 15 mm.

Various thermoplastic resins are suitable for forming shell 34. Example materials include Pellethane™ (a polytetramethylene glycol ether resin available from Dow Chemical Company, such as Pellethane 2363), Pebax™ (a polyether block amide resin available from Atochem, Inc., such as Pebax 2533), PVCs, polyurethanes, and polyethylenes. Each of these materials offer different combinations of characteristics important to the manufacture and operation of fetal probe 10. Some of these characteristics are ease of molding, strength, adhesion to hydrogel, hardness, water absorption, biocompatibility, price, and signal isolation.

Figure 8A:
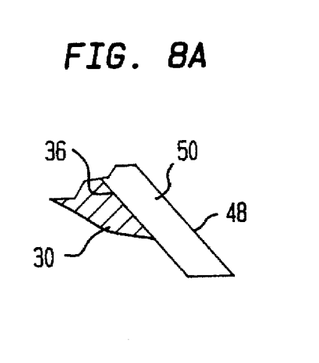
FIG. 8A is a cross section of the wall of the shell shown in FIG. 7, illustrating a straight inner wall surface.
Figure 8B:
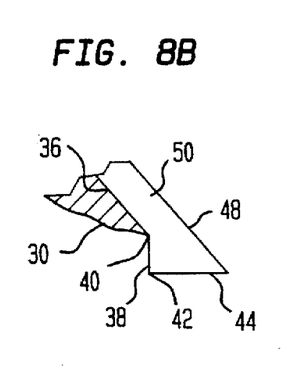
FIG. 8B is a cross section of the wall of the shell shown in FIG. 7, illustrating a ridge.
Figure 8C:
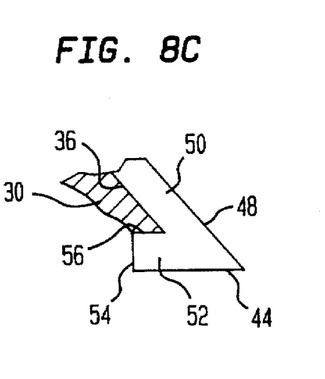
FIG. 8C is a cross section of the wall of the shell shown in FIG. 7, illustrating a ledge.

By using shell 34, the hydrogel of body 30 may be isolated from external fluids. FIGS. 8A, 8B, and 8C show three variations in the configuration of wall 50 of shell 34. FIG. 8A shows a "straight" inner surface 36, without deviations or additions, entirely parallel to the outer surface 48 of wall 50 of shell 34. FIG. 8B shows a ridge 38, which is a straight, vertical segment near the perimeter of wall 50 of shell 34. Ridge 38 has a top edge 40 and a lower edge 42. Top edge 40 is defined by ridge 38 meeting inner wall 36. Lower edge 42 is defined by bottom, horizontal surface 44 of wall 50 meeting ridge 38.

FIG. 8C shows a ledge 52, which is an extension of the wall 50 in a plane which is approximately at a 30-degree angle to outer wall 48 of shell 34. The angle of ledge 52 could be adjusted (at, for example, angles between 15 and 60 degrees) to achieve a desired holding strength. Ledge 52 has a side surface 54 and a top surface 56.

Ridge 38 of FIG. 8B and ledge 52 of FIG. 8C help to isolate the hydrogel of body 30 from external fluids by forming a seal between the hydrogel and external fluids. A fetal probe 10 constructed with ridge 38 remained attached to a simulated test "baby" for more than 32 hours while immersed in an isotonic saline solution. Ledge 52 is advantageous because it allows the hydrogel to be extended closer to the edge of shell 34.

Initial attachment of fetal probe 10 to fetus 100 uses both the vacuum effect (negative pressure) created by the suction cup shape of body 30 of fetal probe 10 and the adhesive properties of the hydrogel adhering to the wet surface of fetus 100 in the uterus. Because hydrogels have shape-retention properties, body 30 retains its suction-cup shape. As the hydrogel absorbs fluid, strong surface adhesive properties are created between the hydrogel and the fetal skin. Air will not seep under the edges of body 30, which would reduce the negative pressure under body 30, because the hydrogel adheres to fetus 100. Thus, suction cup body 30 made of the hydrogel of the present invention exhibits strong adhesive force throughout the duration of labor.

Body 30 of fetal probe 10 has a combined adhesive force generated by the adhesive properties of the hydrogel interface and the concave, suction-cup shape of the interface. Individually, the adhesive force generated by the hydrogel and that generated by the geometry of the interface may be insufficient to secure attachment throughout labor. Although the combined attachment force is sufficient to hold fetal probe 10 in place during labor, it also allows detachment without injury to sensitive fetal tissue. The detachment force of fetal probe 10 from fetal tissue is in the range of 200 g to 2000 g and preferably in the range of 300 g to 1000 g.

C. Fetal Heart Rate Probe

One specific application of fetal probe 10 will be described to better illustrate the advantages of fetal probe 10. Fetal probe 10 may be used to monitor fetal heart rate without penetration of the fetal epidermis. At least four criteria affect the quality of the fetal heart rate signal monitored: (1) symmetry between the fetal and maternal (reference) electrodes, (2) maximum separation between the fetal and reference sensors, (3) maximum surface contact area to minimize impedance, and (4) stabilized connections. Application of fetal probe 10 to monitor fetal heart rate meets these criteria well.

In this application, fetal sensor 12 detects the electrical fetal heart rate signal transcutaneously. To do so, fetal sensor 12 must maintain contact with fetus 100, either directly (FIG. 1) or through the conductive hydrogel of body 30 (FIG. 3). When in direct contact with fetus 100, fetal sensor 12 may be covered with a conductive medium, such as a conductive gel, to lower impedance at the skin-sensor interface. Fetal sensor 12 must provide a sufficiently large surface area and be electrically conductive to sense the electrical fetal heart rate signal. In addition, fetal sensor 12 must be inert to chemical reaction with hydrogel and biological fluids and tissues.

A suitable material for construction of fetal sensor 12 in this application is the silver-silver chloride sensors commonly used in ECG monitoring electrodes. Fetal sensor 12 could also be formed from multi-strand stainless steel wire, such as a Teflon®-coated steel wire sold by Cooner Wire in Chatsworth, Calif. Typically the steel wire is made into a circular loop or helix. In one embodiment, six individual strands of 40-gauge wire were spread over concave surface 32 of body 30 to form fetal sensor 12. Such wire is very fine and light weight; therefore, it adds little mass to fetal probe 10. Alternative insulating jacket materials for the wire, other than Teflon®, could also be used.

Multi-strand carbon fiber wire is a suitable replacement for stainless steel in forming fetal sensor 12. Carbon wires are light weight and flexible. Moreover, they provide good electrical signals and do not react with hydrogel components or saline solutions. Suitable carbon wire can be obtained from Minnesota Wire and Cable Company in St. Paul, Minn.

In this application, fetal connector 14 is a lead wire suitable for conducting the electrical signals from fetal sensor 12 to a monitoring-signal processing unit. Fetal connector 14 passes through body 30 and maternal sensor 16 and is ultimately connected (perhaps through other wires and electrical connections) to a fetal heart rate monitor (monitor 80 shown in FIGS. 1 and 3). The environment in which fetal probe 10 is used, namely inside the uterus, requires insulation of the lead wire. The connection between fetal connector 14 and fetal sensor 12 is embedded in the conductive, adhesive hydrogel of body 30.

In this application, maternal sensor 16 must provide a sufficiently large surface area and be electrically conductive to sense the electrical maternal heart rate signal and other muscular or electrical activity. In addition, maternal sensor 16 must be inert to chemical reaction with biological fluids and tissues. Multi-strand stainless steel or carbon fiber wires, described above for use as fetal sensor 12, can also be used for maternal sensor 16. Alternatively, maternal sensor 16 may be an electrically conducting material such as a metal foil (e.g., silver, aluminum, or stainless steel) or metallized film (e.g., aluminum metallized polyester) or metal wire made into a circular loop or helix (e.g., stainless steel) which covers the upper surface of insulating barrier 20. Other electrically conductive, non-metallic films and coatings such as conductive carbon and conductive graphite may also be used.

Figure 9:
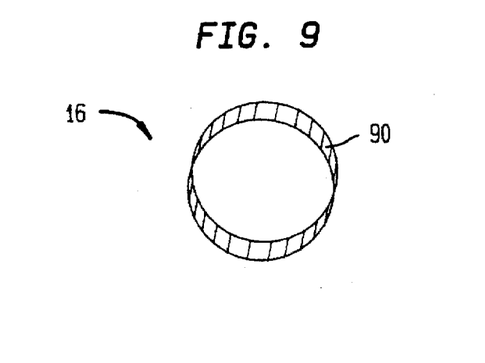
FIG. 9 shows an exemplary embodiment of the maternal sensor incorporated into the fetal probe of FIGS. 1, 3, or 7.

Maternal sensor 16 may be a band, washer, wire loop, or plate which fits on top of body 30 over insulating barrier 20. In an exemplary embodiment, as shown in FIG. 9, stainless steel band 90 can be approximately 3.5 to 4.0 mm wide (preferably 3.7 mm) and 5.0 to 5.5 mm in diameter (preferably 5.4 mm). Maternal connector 18 is a lead wire connected to maternal sensor 16 for communicating received electrical signals.

The maternal heart rate detected by maternal sensor 16 is used as a reference signal so that any maternal heart rate and other muscular or electrical signals which pass through the fetus and are detected by fetal sensor 12 can be subtracted out to provide an accurate fetal heart rate measurement. Generally, the reference component of the signal detected by fetal heart rate sensor 12 is a minor component when compared to the fetal heart rate signal. The fetal heart rate can then be isolated from the combined fetal and reference signals detected by fetal sensor 12. This is accomplished by isolating the fetal R-waves from the other signals.

Non-invasive fetal probe 10 has two leads 14, 18 - - - similar to conventional fetal scalp electrodes-for fetal sensor 12 and maternal reference sensor 16. It is contemplated that both the fetal and maternal leads 14 and 18 could be replaced by a non-wired connecting system, such as a radio transmission system, to communicate information from fetal sensor 12 and maternal sensor 16 to monitoring equipment 80. A radio system would require supporting hardware as is understood by those skilled in the art.

Referring back to FIGS. 1 and 2, insulating barrier 20 serves to maintain electrical insulation between fetal sensor 12 and maternal sensor 16. Pebax, a polyether block amide, is one type of insulating barrier which can serve this purpose. Other similar materials having sufficiently high dielectric properties also would suffice. Insulating barrier 20 should be flexible so as not to impede the flexibility of body 30. Ridge 38 or ledge 52 provided on wall 50 of shell 34 increases the separation of the fetal and maternal signals, which allows monitor 80 to more easily isolate the fetal heart rate signal, and helps to assure electrical isolation between fetal sensor 12 and the external fluid.

When fetal probe 10 is initially applied to fetus 100, the hydrogel of body 30 absorbs moisture and increases in tackiness. Moreover, the hydrogel swells and forces ridge 38 or ledge 52 against fetus 100 - - - enhancing the adhesive seal between fetal probe 10 and fetus 100. Should the hydrogel absorb too much moisture and swell to the extent that it extends under shell 34, however, the seal between fetal probe 10 and fetus 100 may be adversely affected. In addition, the electric isolation between fetal sensor 12 and the external fluid would be jeopardized. Ridge 38 or ledge 52 helps to isolate the hydrogel from external fluids, thereby preventing the hydrogel from absorbing too much moisture and risking such adverse consequences.

FIGS. 1 and 3 illustrate fetal probe 10 connected to a signal processing and display unit 80. Signal processing and display unit 80 is used, in this application, to monitor the fetal heart rate detected by fetal probe 10. Signal processing display unit 80 contains the digital signal processing equipment and control instructions necessary to discriminate the fetal heart rate signal from the other extraneous signals. Signal processing display unit 80 may also carry out, in other applications for fetal probe 10, blood gas analysis, oximetry measurements, and other functions.

III) Fetal Pulse Oximeter Using the Wet-Adhesive Hydrogel

A second embodiment which uses the wet adhesive hydrogels of the present invention is a fetal pulse oximeter used to monitor the oxygen saturation in fetal tissue during labor. The oximeter uses the wet adhesive hydrogel to hold the sensor on the fetal tissue during labor and delivery. When used in this manner, the hydrogels of the present invention eliminate the trauma to the fetus caused by prior art attachment means such as sharpened wires. Moreover, a hydrogel fetal pulse oximeter is less bulky than current fetal pulse oximeters and easier to manufacture and, therefore, lower in cost. The fetal pulse oximeter uses conventional semiconductors such as photodiodes and photo detectors or fibre optic sensors for detecting the pulsed ratio of hemoglobin and oxyhemoglobin in fetal blood.

An example of such an oximeter is described in German Patent Application Number P4304693.2. This oximeter senses pulsatile hemoglobin and oxyhemoglobin using semiconductors which can be attached to the fetal scalp with a sharpened helix wire or other adhesive means. The hydrogel compositions of the present invention having wet adhesive properties, preferably those conductive compositions disclosed for the body used in the non-invasive fetal probe discussed above, are advantageous for this application. Salient features of such an oximeter are discussed below.

Figure 10:
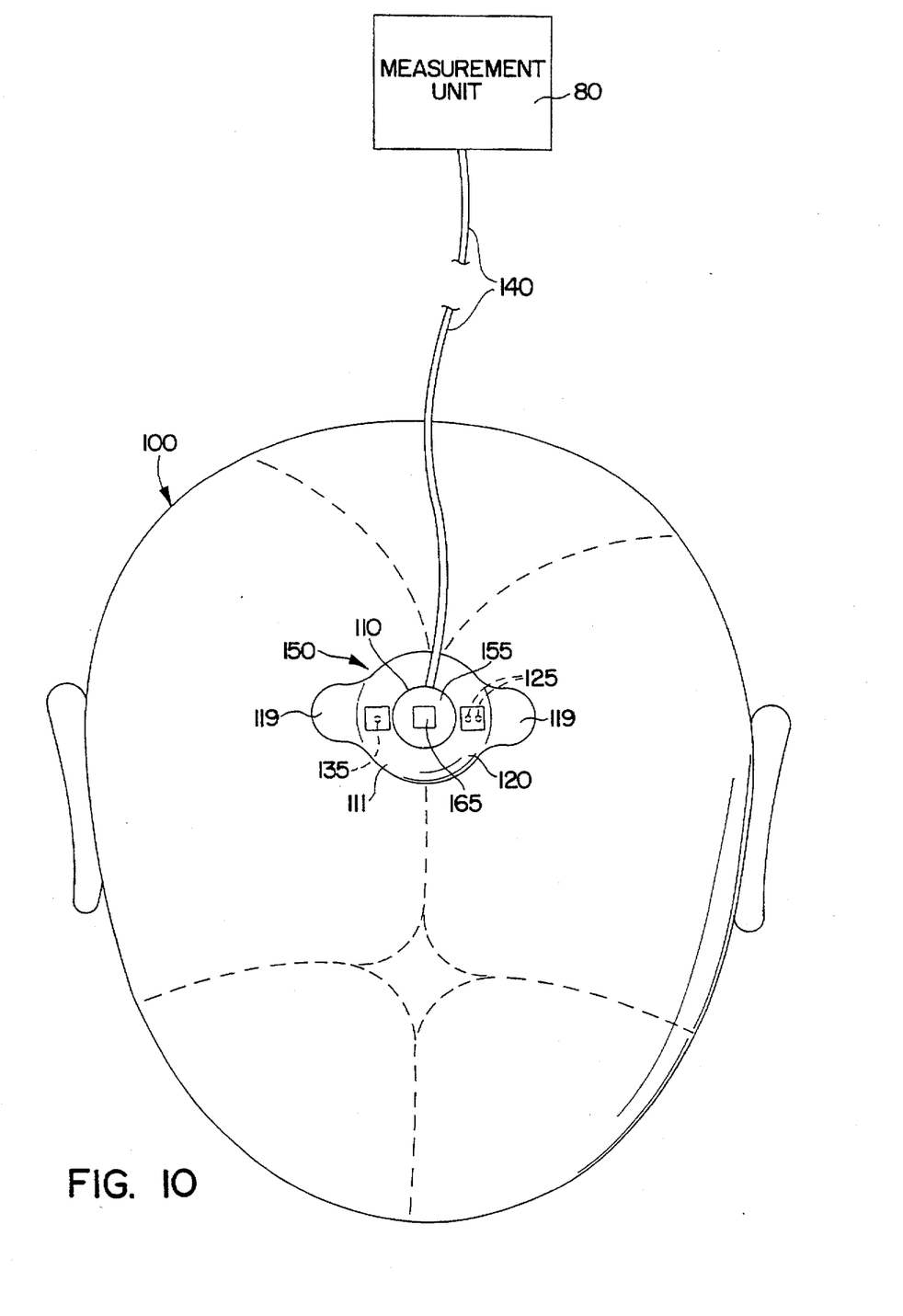
FIG. 10 shows a top view of the carrier (sensor) attached to the head of the fetus in combination with the measurement unit shown on an enlarged scale.
Figure 11:
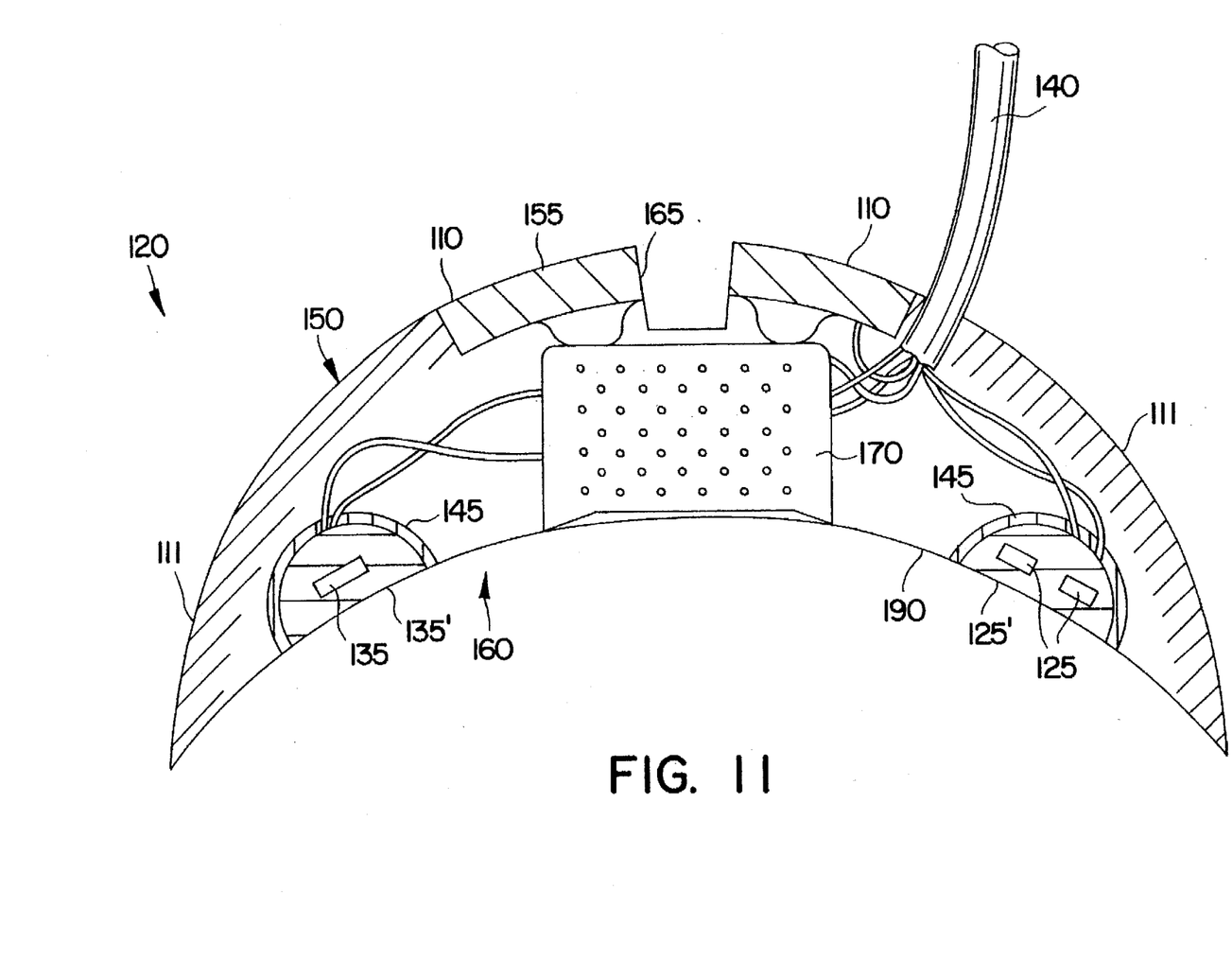
FIG. 11 shows an axial section through the undeformed carrier, greatly enlarged.
Figure 12:
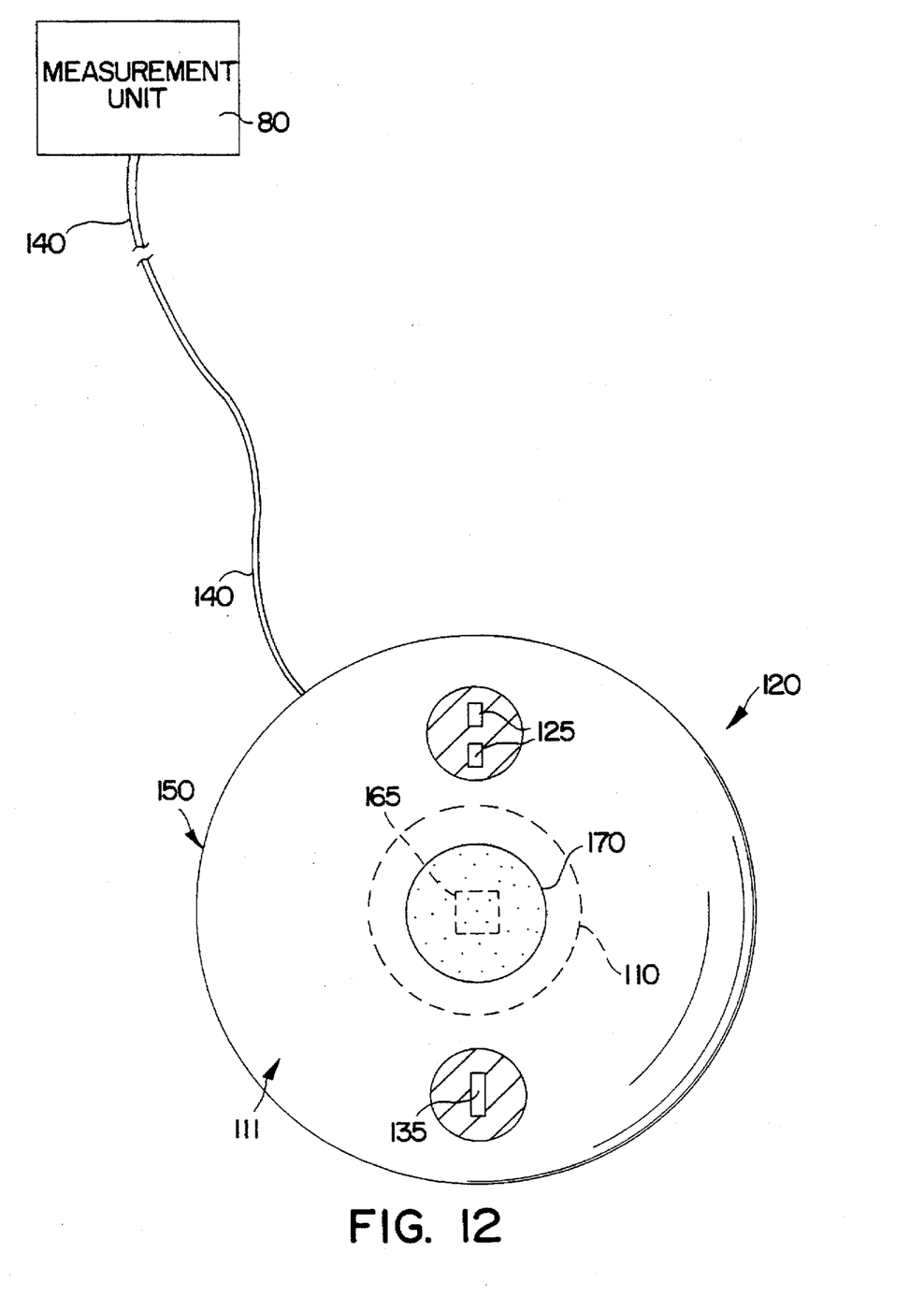
FIG. 12 shows a view of the bottom of the carrier (sensor), greatly enlarged, with the use of the hydrogel of the present invention to attach the carrier to the fetus.

Referring now to FIGS. 10 to 12, wherein like reference numerals refer to like elements, FIG. 10 shows the presenting part of the fetus 100 in delivery, namely the head in the example shown. The mother's birth canal has been omitted for reasons of simplicity. The sensor 120 is inserted through the vagina of a woman in labor and attached to fetus 100. Sensor 120 is connected to measurement unit 80 by lines (electric wires) labeled as 140 in general.

FIG. 11 shows the sensor 120 not attached to the head of fetus 100 so, therefore, it is not deformed. Sensor 120 is typically a round cup 150 made of a relatively soft rubbery material with a curved cross section that tapers significantly toward the edge. Cup 150 has a concavity 160 on the concave side facing the head of fetus 100. A body 170 made of the biocompatible hydrogel of the present invention is located in the center of cup 150 and projects sufficiently out of the surface 190 of concavity 160 in order to contact and adhere to the head of fetus 100 to be monitored. Body 170 can be formed into a flat, suction cup, or other configuration. Sensor 120 thus has a centrally arranged attachment zone 110.

Attachment zone 110 is surrounded by an elastic peripheral zone 111 where a light emitter 125 and a receiver 135 that are embedded in the material of peripheral zone 111 are arranged, whereby their surfaces 125' and 135' are approximately flush with the surface 190 of concavity 160. The curvature of the concavity 160 of cup 150 in the undeformed state is larger than the largest curvature of a fetal head according to statistics.

The light emitter 125 and the receiver 135 are each shielded optically at the rear by a cap 145 within cup 150. At the same time, the surface 190 of concavity 160 has a color that is impermeable for the wavelength of light used in the device or a color that absorbs that wavelength of light.

As shown in FIG. 11, cup 150 is provided on its convex side with a metal plate 155 that is partially embedded in the material of cup 150 and is permanently connected there to body 170. Metal plate 155 forms a structural unit with an internal polygon 165 arranged in the center which serves as a driving portion for moving the hydrogel body 170 against the head of the fetus 100.

Lines 140 may pass through the coupling part - - - in other words, at the center of cup 150 - - - in order to prevent lines 140 from exerting any torque on cup 150, whether when attaching it to fetus 100 or during delivery. One separate line 140 leads to the metal plate 155 and another leads to the conductive hydrogel body 170, so these parts can serve directly as ECG electrodes.

FIG. 12 shows a bottom view of sensor 120, greatly enlarged, having body 170 formed from the hydrogel of the present invention. Light emitter 125 and receiver 135 are linearly aligned and are each connected to measurement unit 80 by their own lines (electric wires) 140. The function and operation of the sensor device is explained below.

The small dimensions of the sensor 120 and its ease of handling permit sensor 120 to be introduced through the vagina and attached to the presenting part of the fetus at a very early stage of labor. To do so, sensor 120 is pressed lightly at the center against the head of fetus 100, for example, by a moving forward a handle having a polygonal profile (not shown) on the distal end that fits into the polygonal profile 165 of cup 150.

Body 170 is pressed onto the fetal tissue by a forward motion of sensor 120. Since body 170 attaches without invading the fetal tissue, no impairment in the fetal tissue is caused. The forward force is transmitted directly by way of the polygonal profile and metal plate 155 to body 170.

When sensor 120 is pressed at the center against the fetal tissue, the peripheral zone 111 of cup 150 is the first to come in contact with the fetal tissue. The peripheral zone 111 then undergoes elastic deformation and the curvature of cup 150 is reduced. The hydrogel adhesive permits the peripheral zone 111 of cup 150 to yield in an elastic, spring-loaded manner when sensor 120 is pressed against the fetal tissue such that peripheral zone 111 rests on the fetal tissue with a slight initial tension. When body 170 has been pressed onto the fetal tissue, the slight initial tension caused by peripheral zone 111 of cup 150 on the fetal tissue causes the surfaces of light emitter 125 and receiver 135 to be in contact with the fetal tissue.

Attachment zone 110 is also pressed by body 170 against the fetal tissue. The pressing of sensor 120 against the fetal tissue thus takes place very gently but tightly at the center as well, but in any case this prevents any impairment of the fetal arterial blood flow in the area of peripheral zone 111.

As shown in FIG. 10, a tab-shaped ear 119 that projects radially outward beyond cup 150 and covers the fetal tissue in this area to prevent light from entering or being emitted can be attached in the area of emitter(s) 125 and/or receiver (s) 135. The light propagates radially beyond the area of cup 150 in an area of approximately 8 mm in the fetal tissue. Therefore, it is advantageous to cover this area with ears 119.

The attachment of sensor 120 to the fetal tissue using the conductive hydrogel of the present invention permits parts which are electrically insulated with respect to each other, namely metal plate 155 and body 170, to be used as electrodes, for example, as ECG electrodes.

The especially simple design of sensor 120 and its very small shape should be emphasized. Sensor 120 can be produced very easily and economically (as a disposable item). Nevertheless, sensor 120 fulfills the need for a non-invasive, reliable, and durable means of attachment to the fetal tissue and satisfactory reception of signals for the purpose of measuring vital parameters of a fetus during labor and delivery.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. In a process for producing a medical device attaching to a patient, the improvement comprising the steps of:
   applying a coating of a precursor composition comprising acrylic acid monomer and an alcoholamine to said medical device; and
   polymerizing said precursor composition to produce a hydrogel which is adhesive under both wet and dry conditions.

2. A process as recited in claim 1 wherein said alcoholamine is diisopropanolamine.

3. A process as recited in claim 2 wherein said device is a fetal pulse oximeter sensor attaching to a presenting part of a fetus and monitoring at least one fetal parameter during labor and delivery.

4. A process as recited in claim 2 wherein said precursor further comprises water, a photoinitiator, and a crosslinking agent.

5. A process as recited in claim 4 wherein said device is a fetal pulse oximeter sensor attaching to a presenting part of a fetus and monitoring at least one fetal parameter during labor and delivery.

6. A process as recited in claim 2 wherein said precursor comprises up to about 40% water, up to about 30% acrylic acid, 0.3–0.4% photoinitiator, 0.05–0.20% crosslinking agent, and up to about 30% diisopropanolamine.

7. A process as recited in claim 6 wherein said precursor comprises about 29% water, about 25% acrylic acid, about 0.35% 2-hydroxy-2-methyl-1-phenyl-propane-1-one, about 0.10% polyethylene glycol (400) diacrylate, and about 24% diisopropanolamine.

8. A process as recited in claim 6 wherein said precursor comprises about 39% water, about 29% acrylic acid, about 0.35% 2-hydroxy-2-methyl-1-phenyl-propane-1-one, about 0.10% polyethylene glycol diacrylate, and about 28% diisopropanolamine.

9. A process as recited in claim 6 wherein said precursor comprises about 35% water, about 18% acrylic acid, about 0.35% 2-hydroxy-2-methyl-1-phenyl-propane-1-one, about 0.10% polyethylene glycol (400) diacrylate, and about 30% diisopropanolamine.

10. A process as recited in claim 6 wherein said precursor comprises about 39% water, about 16% acrylic acid, about 0.35% 2-hydroxy-2-methyl-1-phenyl-propane-1-one, about 0.15% polyethylene glycol (400) diacrylate, about 28% diisopropanolamine, and about 13.0% vinyl pyrrolidone.

11. A process as recited in claim 6 wherein said precursor comprises about 25% water, about 19% acrylic acid, about 0.35% 2-hydroxy-2-methyl-1-phenyl-propane-1-one, about 0.10% polyethylene glycol (400) diacrylate, and about 8% diisopropanolamine.

12. A process as recited in claim 6 wherein said precursor comprises about 11% water, about 22% acrylic acid, about 0.33% 2-hydroxy-2-methyl-1-phenyl-propane-1-one, about 0.17% polyethylene glycol (400) diacrylate, and about 14% diisopropanolamine.

13. A process as recited in claim 6 wherein said precursor comprises about 38% water, about 16% acrylic acid, about 0.35% 2-hydroxy-2-methyl-1-phenyl-propane-1-one, about 0.15% polyethylene glycol (400) diacrylate, about 28% diisopropanolamine, and about 13% vinyl pyrrolidone.

14. A process as recited in claim 6 wherein said device is a fetal pulse oximeter sensor attaching to a presenting part of a fetus and monitoring at least one fetal parameter during labor and delivery.

15. A process as recited in claim 1 wherein said hydrogel is conductive.

16. A process as recited in claim 1 wherein said device is a non-invasive fetal probe attaching to a presenting part of a fetus and monitoring at least one fetal parameter during labor and delivery, said probe comprising:
   a body having a surface adapted for securing the probe to the fetus to be monitored, said body comprised of said hydrogel which is adhesive under both wet and dry conditions;
   a sensor carried by said body and detecting at least one fetal parameter; and means for communicating the fetal parameter detected by said sensor from said sensor to a monitor.

17. A process as recited in claim 16 wherein said body of said non-invasive fetal probe has a diameter of 10–20 mm.

18. A process as recited in claim 16 wherein said body of said non-invasive fetal probe is comprised entirely of said hydrogel.

19. A process as recited in claim 16 wherein said body of said non-invasive fetal probe further comprises a shell, and said hydrogel is coated on said shell and forms said concave surface of said body facing the fetus.

20. A process as recited in claim 19 wherein said shell of said non-invasive fetal probe is polymeric.

21. A process as recited in claim 19 wherein said shell of said non-invasive fetal probe has an outer perimeter forming a member which is one of a ledge and a ridge isolating said hydrogel from fluids in the environment surrounding the probe.

22. A process as recited in claim 21 wherein said member formed by said outer perimeter of said shell is a ridge having a top edge and a lower edge and wherein said hydrogel extends to said top edge of said ridge.

23. A process as recited in claim 21 wherein said member formed by said outer perimeter of said shell is a ledge having a side surface, a top surface, and a bottom surface and wherein said hydrogel is disposed on said top surface.

24. A process as recited in claim 1 wherein said device is a fetal pulse oximeter sensor attaching to a presenting part of a fetus and monitoring at least one fetal parameter during labor and delivery.

25. A process as recited in claim 24 wherein said hydrogel is a suction cup.

26. The product produced by the process recited in claim 1.

27. A process for producing a hydrogel adhesive comprising the steps of:

providing a precursor composition comprising acrylic acid monomer and an alcoholamine; and polymerizing said precursor composition to produce a water-insoluble hydrogel adhesive which is adhesive under both wet and dry conditions.

28. A process as recited in claim 27 wherein said alcoholamine is diisopropanolamine.

29. The product produced by the process recited in claim 27.

30. A process for producing a hydrogel adhesive comprising the steps of:

providing a precursor composition comprising acrylic acid, diisopropanolamine, water, a photoinitiator, and a crosslinking agent; and polymerizing said precursor composition to produce a hydrogel adhesive which is adhesive under both wet and dry conditions.

31. A process as recited in claim 30 wherein said precursor further comprises an electrolyte.

32. A process for producing a hydrogel adhesive comprising the steps of:

providing a precursor composition comprising up to about 40% water, up to about 30% acrylic acid, 0.3–0.4% photoinitiator, 0.05–0.20% crosslinking agent, and up to about 30% diisopropanolamine; and polymerizing said precursor composition to produce a hydrogel adhesive which is adhesive under both wet and dry conditions.

33. A process as recited in claim 32 wherein said precursor comprises about 29% water, about 25% acrylic acid, about 0.35% 2-hydroxy-2-methyl-1-phenyl-propane-1-one, about 0.10% polyethylene glycol (400) diacrylate, and about 24% diisopropanolamine.

34. A process as recited in claim 32 wherein said precursor comprises about 39% water, about 29% acrylic acid, about 0.35% 2-hydroxy-2-methyl-1-phenyl-propane-1-one, about 0.10% polyethylene glycol (400) diacrylate, and about 28% diisopropanolamine.

35. A process as recited in claim 32 wherein said precursor comprises about 35% water, about 18% acrylic acid, about 0.35% 2-hydroxy-2-methyl-1-phenyl-propane-1-one, about 0.10% polyethylene glycol (400) diacrylate, and about 30% diisopropanolamine.

36. A process as recited in claim 32 wherein said precursor comprises about 39% water, about 16% acrylic acid, about 0.35% 2-hydroxy-2-methyl-1-phenyl-propane-1-one, about 0.15% polyethylene glycol (400) diacrylate, about 28% diisopropanolamine, and about 13.0% vinyl pyrrolidone.

37. A process as recited in claim 32 wherein said precursor comprises about 25% water, about 19% acrylic acid, about 0.35% 2-hydroxy-2-methyl-1-phenyl-propane-1-one, about 0.10% polyethylene glycol (400) diacrylate, and about 8% diisopropanolamine.

38. A process as recited in claim 32 wherein said precursor comprises about 11% water, about 22% acrylic acid, about 0.33% 2-hydroxy-2-methyl-1-phenyl-propane-1-one, about 0.17% polyethylene glycol (400) diacrylate, and about 14% diisopropanolamine.

39. A process as recited in claim 32 wherein said precursor comprises about 38% water, about 16% acrylic acid, about 0.35% 2-hydroxy-2-methyl-1-phenyl-propane-1-one, about 0.15% polyethylene glycol (400) diacrylate, about 28% diisopropanolamine, and about 13% vinyl pyrrolidone.

* * * * *

UNITED STATES PATENT AND TRADE MARK OFFICE
CERTIFICATE OF CORRECTION

PATENT NO. : 5,665,477
DATED : September 9, 1997
INVENTOR(S) : Meathrel et al.

It is certified that error appears in the above-identified patent and that said Letters Patent is hereby corrected as shown below:

Col. 2, line 36, after "polymer" insert comma.

In Col. 4, line 29, in the equation, "$R^c$" should be "$R^v$".

In Col. 9, line 25, the word "adhesive's" should be "adhesives".

In Col. 10, line 22, in Table 3, "Shave" should be "Shape".

In Col. 13, line 22, " delete comma before "probe".

In Col. 16, Claim 8, line 27, after "glycol" insert "(400)".

Signed and Sealed this

Twenty-fourth Day of March, 1998

*Attest:*

BRUCE LEHMAN

*Attesting Officer*  *Commissioner of Patents and Trademarks*